(12) United States Patent
Eckhardt et al.

(10) Patent No.: US 6,652,281 B1
(45) Date of Patent: Nov. 25, 2003

(54) DENTAL MATERIALS

(75) Inventors: Gunther Eckhardt, Frieding (DE); Thomas Luchterhandt, Krailling (DE); Thomas Klettke, Hechendorf (DE)

(73) Assignee: 3M ESPE AG, Seefeld (DE)

(*) Notice: Subject to any disclaimer, the term of this patent is extended or adjusted under 35 U.S.C. 154(b) by 0 days.

(21) Appl. No.: 09/959,102

(22) PCT Filed: Apr. 25, 2000

(86) PCT No.: PCT/EP00/03676

§ 371 (c)(1),
(2), (4) Date: Feb. 5, 2002

(87) PCT Pub. No.: WO00/66069

PCT Pub. Date: Nov. 9, 2000

(30) Foreign Application Priority Data

Apr. 29, 1999 (DE) .......................... 199 19 581

(51) Int. Cl.⁷ .............................. A61C 13/23
(52) U.S. Cl. ................. 433/219; 433/217.1; 433/222.1; 433/226; 433/228; 526/197; 526/198; 526/222; 528/88; 528/90; 528/91
(58) Field of Search ............................. 528/88, 90, 91; 526/197, 198, 222; 433/217.1, 219, 222.1, 226, 228.1

(56) References Cited

U.S. PATENT DOCUMENTS 4,656,229 A * 4/1987 Chiao .................... 525/518

FOREIGN PATENT DOCUMENTS

| DE | 3201780 | 8/1983 |
|----|---------|--------|
| DE | 3939164 | 5/1991 |
| DE | 19736471 | 2/1999 |
| EP | 0985684 | 3/2000 |
| GB | 1113722 | 5/1968 |
| WO | WO 9817694 | 4/1998 |

* cited by examiner

Primary Examiner—Robert Dawson
Assistant Examiner—D. Aylward
(74) Attorney, Agent, or Firm—Crowell & Moring LLP

(57) ABSTRACT

Dental materials containing monomers and/or prepolymers can be subjected to a polymer-forming reaction. The dental materials comprise at least one initiating system and optionally comprise fillers, colorants, flow modifiers, stabilizers, ion-releasing substances as well as compounds which increase X-ray capacity or other modifiers. The dental materials are characterized in that the initiating system is proportioned such that the dental materials are sufficiently capable of flowing for at least 10 seconds after exposure to oxygen, whereupon they subsequently harden into a solid material.

25 Claims, No Drawings

DENTAL MATERIALS

For some time the goal in dental medicine has been to replace the classical filling material amalgam with composites ("plastics"). In contrast to amalgam, it is necessary in the provision with composites to use a bonding agent. This so-called bonding is applied on the prepared hard tooth substance prior to the insertion of the composite into the cavity.

One important requirement of users of dental materials is that the processing be as simple as possible, that the processing not allow any processing errors and that the desired results are always the same.

This requirement can be fulfilled at least to some degree when single component dental materials are prepared and processed.

The use of single component dental materials assumes that the polymer-forming reaction can be initiated either by supplying energy and/or through reaction with components of "active" surfaces or the surrounding atmosphere.

A typical case for the initiation of polymerization through the supply of energy is photo-induced curing of dental materials, where irradiation with light causes the decomposition of the photo initiators into polymerization initiating species.

The curing rate of such photocuring dental materials is generally very high, but curing takes place only in the areas reached by the light.

Due to the short lifespan of the polymerization initiating species, like the free radicals, it is usually only possible to realize the exposure and thus the curing at the site of the end use of the cured dental material.

This circumstance restricts the use of photocuring for dental materials. Therefore, dental materials are desired that exhibit, as single component preparations, an adequate shelf life and that can be easily "activated".

In this respect "activability" means that the polymerization initiating species are produced in the dental materials taken from the storage container through the introduction of energy and/or through reaction with components having "active" surfaces or the surrounding atmosphere, provided that the dental materials can flow adequately freely for at least another 10 seconds following "activation" in order to guarantee an application as intended.

Therefore, the object is to propose single component dental materials that exhibit stability in storage and an adequately long processing period after "activation".

The problem of the invention is solved by dental materials, containing monomers and/or prepolymers that are capable of a polymer-forming reaction; at least one initiating system, and optionally fillers, dyes, flow modifiers, stabilizers, ion-transferring substances, the x-ray opacity-increasing compounds or other modifiers, which are characterized in that the initiating system is produced in such a manner that, when brought into contact with oxygen, it releases species initiating the polymer-forming reaction; and the quantity of initiating system is dimensioned in such a manner that after bringing into contact with oxygen the dental materials can flow adequately freely and can be processed for at least another 10 seconds and thereafter cure to a solid.

The resulting smear layer is preferably less than 0.2 mg/cm$^2$.

According to the invention, an oxygen sensitive compound is used, that when brought into contact with oxygen, can form an excited or reactive species, preferably radicals that in turn can release acid from a saline initiator by means of another reaction sequence. Said acid can initiate a polymerization reaction, in particular a cationic polymerization reaction.

This saline initiator is, for example, iodonium compounds, which, when activated, for example, by means of free radicals, can decompose into acids.

Thus, there are two initiator systems, which react with each other, to control the course of the polymerization reaction.

According to a preferred embodiment of the invention, the dental materials are taken from the sealed, oxygen-impermeable storage container and brought into contact with the ambient air within a period ranging from 1 to 120 seconds. At the same time it is expedient to provide new surfaces by filling and slightly mixing, a feature that accelerates the "activation".

According to another embodiment of the invention, the dental materials are applied on "active" surfaces that release oxygen, whereby the oxygen can be produced, for example, through reaction of a compound, located on the surface, with a component of the liquid dental materials.

The dental materials, according to the invention, cure so as to form a polymer, whereby preferably such monomers or prepolymers are used that polymerize according to a cation chain mechanism, by means of a thiol-ene mechanism or according to a radical chain mechanism.

Combinations of several mechanisms are also possible.

Thus, the dental materials can contain monomers and prepolymers that cure by means of ring-opening polymerization, whereby the use of compounds containing at least two epoxide groups is preferred. Cycloaliphatic epoxide resins, which cure according to a cationic ring opening mechanism, constitute a class of monomers that can be used advantageously.

Typical representatives of these cycloaliphatic epoxide resins are described, for example, in the DE-A-196 48 283 A1.

The dental preparations, which cure according to a thiol-ene mechanism, contain multi-thiol compounds, like the tetramercaptopropionate of pentaerythritol, and multi-allyl compounds, like triallyl isocyanurate.

Such dental materials, based on thiol-ene systems, are described in detail in the DE-A 3837569, to which reference is made here.

Typical monomers or prepolymers that cure according to a radical chain mechanism and are used in dental materials are acrylates or methacrylates. Suitable are generally uni- or multi-functional (meth)acrylate monomers. Typical representatives of this class of compounds are alkyl(meth)acrylates, including cycloalkyl(meth)acrylates, aralkyl (meth)acrylates and 2-hydroxyalkyl(meth) acrylates, like hydroxypropyl methacrylate, hydroxyethylmethacrylate, isobornyl acrylate, isobornyl methacrylate, butyl glycol methacrylate, acetyl glycol methacrylate, triethylene glycol dimethacrylate, polyethylene glycol dimethacrylate, 2-phenylethylmethacrylate, 2-ethylhexyl methacrylate, cyclohexyl methacrylate, lauryl methacrylate and hexanedioldi(meth)acrylate, as described in the DE-A 4328960.

Long chained monomers, based on bisphenol A and glycidyl methacrylate or their derivatives, produced through the addition of isocyanates, as described in the U.S. Pat. No. 3,066,112, can also be used. Suitable are also the compounds of the type bisphenyl-A-diethyloxy(meth)acrylate and bisphenol-A-dipropyloxy(meth)acrylate.

Furthermore, the oligoethoxylated and oligopropoxylated bisphenol-A-diacrylic and dimethacrylic acid esters can be used. Quite suitable are also the diacrylic and dimethacrylic acid esters, which are mentioned in the DE-C 2816823 and belong to bis(hydroxymethyl)-tricyclo $[5.2.1.0^{2,6}]$-decane, and the diacrylic and dimethacrylic acid esters of the compounds of bis(hydroxymethyl)-tricyclo $[5.2.1.0^{2,6}]$-decane, which are extended with 1 to 3 ethylene oxide and/or propylene oxide units. This list is intended as an example and not to be understood as conclusive by any means.

Mixtures of the aforementioned monomers can also be used.

The inventive dental materials contain at least one initiating system, which upon contact with oxygen releases the species initiating the polymer-forming reaction.

Preferably the dental materials contain compounds, which are rapidly oxidized by means of oxygen, whereby free radicals are formed by this reaction or by successive reactions. Said free radicals initiate either directly the polymer formation or form, after reaction with other components of the liquid dental preparations, the species initiating the polymer-forming reactions.

Suitable classes of compounds subject to rapid oxidation by means of oxygen are, for example, substituted hydrazones and boranes.

Thus, the autoxidation of hydrazones is already described in the Report 47 (1994) pp. 3277 to 3291.

Hydrazones-containing multicomponent mixtures, which are capable of undergoing free radical polymerization by means of the addition of atmospheric oxygen, are described in the DE-A 4000776, column 2 (line 67) to column 9 (line 41), to which explicit reference is made with respect to the disclosure.

Preferably the hydrazone compounds, described in the EP-A 0510035 and in the EP-A 0594671, can also be used. These hydrazones are capable of forming hydroperoxides and are usually used as polymerization starters for monomers that are capable of undergoing free radical polymerization.

In a preferred embodiment of the present invention hydrazones of the described type are used together with iodonium compounds, in particular bisaryliodonium salts of stronger acids, to cure preparations containing epoxide group-containing monomers.

The DE-A 3041904 describes boron compounds-containing plastic compounds that cure after making contact with oxygen and that are used especially as reaction adhesives.

In the DE-A 3201780 new polymeric organoboron compounds are proposed that impart to the multicomponent mixtures, which are capable of undergoing free radical polymerization, an improved stability during high initiating action.

The EP-A 0835646 describes adhesive compositions, which contain organic boron compounds and can be used, among other things, in dental materials, like bondings.

A common feature of the aforementioned proposed solutions is that they relate exclusively to free radical curing preparations and that the important demand of users of dental materials for a preparation that is as simple as possible and for constancy of preparation results is fulfilled to a very limited degree.

The inventive preparations and processing techniques expand the possible polymer-forming reactions by the cationic ring opening polymerization and thiolene systems, thus achieving adequate shelf life and simple processability.

In preparations, which are capable of free radical polymerization, properties extending far beyond those described in the state of the art are obtained.

With the use of monomers or prepolymers, which cure by means of a cationic ring opening polymerization, not only compounds reacting with oxygen, like hydrazones or boranes, but also the presence of compounds that decompose under the influence of radicals so as to form acids are necessary.

For this embodiment of the invention, acid formers, as described in detail in the DE-A 19736471, have proved to be especially appropriate.

Based on the total preparation, the inventive dental materials usually contain 0.1 to 10% by weight, preferably 0.2 to 5% by weight and especially preferred 0.5 to 3% by weight of initiator, and based on the total preparation, usually 90 to 99.9% by weight, preferably 95 to 99.8% by weight and especially preferred 97 to 99.5% by weight of monomers or prepolymers or their mixtures.

When this combination of compounds is used, it is also possible to cure monomer mixtures that contain substances, which are capable of undergoing only free radical or only cationic polymerization, and that contain both classes of substances.

The dental materials, according to the invention, may or may not contain fillers, dyes, flow modifiers, stabilizers, ion-transferring substances, the x-ray opacity increasing compounds, or other modifiers.

Suitable fillers are, for example, substances, described in the DE-A 19648283 (page 10, lines 48–59).

When the inventive dental materials contain fillers, they comprise:
a) preferably 0.1 to 10% by weight, in a more preferred manner 0.2 to 5% by weight and in an especially preferred manner 0.5 to 3% by weight initiator,
b) preferably 3 to 84.9% by weight, in a more preferred manner 5 to 75% by weight and in an especially preferred manner 20 to 75% by weight fillers,
c) preferably 15 to 96.9% by weight, in a more preferred manner 20 to 94.8% by weight and in an especially preferred manner 22 to 79.5% by weight monomers or prepolymers or their mixtures.

If in addition the compositions contain one or more of the aforementioned additional additives, like dyes, flow modifiers etc., they are present in quantities that are customary in the dental sector.

One special advantage of the inventive preparations and processing techniques lies in the fact that the range of the "activation time" and the "processing time" is determined by the composition of the activable dental materials; and the processor can influence within specific limits the requisite "processing time" by means of the intensity with which said materials are brought into contact with oxygen or air.

The dental materials, according to the invention, are packed into suitable containers, which are preferably oxygen and light impermeable, for use according to the instructions. Suitable containers are cartridges, mixing capsules, compules, or tubes.

EXAMPLES

Embodiment 1

In a triple arm kneader the substances, described below, are kneaded into a homogeneous paste under nitrogen in a dark room.

The paste is evacuated; the vacuum is filled with nitrogen and the paste is put into light and oxygen impermeable dosing containers.

| Composition of the paste: | Gram based on 100 g of paste |
|---|---|
| bis(4-dodecylphenyl)iodoniumtetracis(pentafluoro-phenyl)borate | 0.62 |
| 3,4-epoxycyclohexylmethyl-3,4-epoxycyclohexylcarboxylate | 14.19 |
| 1,3,5,7-tetracis-(2,1-ethanediyl-3,4-epoxycyclohexyl)-1,3,5,7-tetramethylcyclotetrasiloxane | 7.81 |
| quartz, average particle size 2 micrometers, silanized with epoxysilane | 66.51 |
| tributylborane* | 0.47 |
| 2-butoxyethyl-4-dimethylaminobenzoate | 0.08 |
| dilithiumcarboxylate of a polyethylene glycol 600 diacid | 0.11 |
| bisphenol-A-monoglycidether monomethacrylate (UVACURE 1561) | 10.21 |

*Polymeric boron alkyl B2, prepared according to the data in Table B of the DE-A 3201780.

The paste was used to cement crowns.

To this end, 0.3 g of the paste was removed from the dosing container and put on a silicone paper block, slightly kneaded with the spatula for 20 seconds, filled into the crown and the filled crown is mounted on the prepared stump.

The projecting paste could be easily removed after 2 minutes.

The cemented crown was functional ten minutes after mounting on the stump.

In light and oxygen impermeable dosing containers the product is stable in storage for 18 months.

Another application of the inventive preparations is in the area of temporary crowns and bridges. The dentist prepares them usually in such a manner that before the preparation he takes an impression of the momentary tooth situation, for example, with a silicone precision impression material.

Following preparation of the tooth or the teeth, they need temporary protection and are provided with a temporary crown or bridge. To this end, the situation impression is filled with an appropriate material, the mixed temporary crown and bridge material. Then the filled impression is put on the prepared tooth stump and cured up to the elastic phase in the mouth. During the elastic phase the material is removed and allowed to stand at room temperature until it is completely cured. After curing, the material usually exhibits a so-called "smear layer". It is usually created by means of oxygen on the surface in connection with the inhibition of radical polymerization.

Before the dentist can continue to process the temporary structure, the smear layer has to be removed, a step that means a considerable amount of work. The use of the preparations, according to the invention, has demonstrated that virtually no smear layer is created and thus this significant drawback has been eliminated. The preparations, listed below, are embodiments and do not by any means constitute restrictions.

Embodiment 2

Two component material for temporary crowns and bridges, which is mixed in a ratio of 10/1 (base/catalyst) and cured without any smear layer.

The base paste and the catalyst paste are admixed from the components, listed in Table 1, under nitrogen by means of kneading.

| | Gram, based on 100 g of paste: |
|---|---|
| Base paste: | |
| pyrogenic silicic acid (particle size < 0.05 micrometers) | 5.00 |
| glass powder, silanized (average particle size 10 micrometers) | 32.50 |
| 2,2-bis(4-(oligo(ethoxy))-phenyl)propanedimethacrylate | 61.48 |
| N,N-dimethyl-p-toluidine | 0.50 |
| hydroquinone monomethyl ether | 0.02 |
| tributylborane* | 0.50 |
| Catalyst paste: | |
| glass powder, silanized (average particle size 10 micrometers) | 32.00 |
| 2,2-bis(4-(oligo(ethoxy))-phenyl)-propane diacetate | 65.50 |
| benzoylperoxide (peroxide chemistry) | 2.50 |

*Polymeric boron alkyl B2, prepared according to the data in Table B of the DEA 3201780.

The use of the temporary crown and bridge preparation, according to embodiment 2, results in a "total smear layer", for which a numerical value of <0.2 mg/cm$^2$ was found in accordance with the detection limit of the method described below.

Comparison Example 1

With the use of a silicone impression material, a commercial, free radical curing temporary material shows a smear layer (for determination see below) on both the temporary material (approx. 1.6 mg/cm$^2$) and the impression material (approx. 1.2 mg/cm$^2$). The "total smear layer" yields a numerical value of approximately 2.8 mg/cm$^2$.

Method for Determining the Smear Layer

The smear layer is determined as follows:

A Delrin ring (DuPont) (d=20 mm; h=3.5 mm) is placed on a platelet made of the impression material (AP), filled with the sample material (PM) without bubbles, covered with a microscope slide, and cured at room temperature for one hour. After the slide is removed, the test specimen is pushed out, and the sample material and the impression material with the smear layer are weighed (yields m1 and m2).

Then the smear layer is removed from the AP and PM with paper moistened with ethanol. The weighing yields the mass of AP and PP without smear layer (m3 and m4). The total smear layer is derived from:

$$S = \frac{m(a) - m(b)[\text{mg}]}{F[\text{cm}^2]}$$

m(a) : m1+m2 (total mass (AP+PP) with smear layer)
m(b): m3+m4 (total mass (AP+PP) without smear layer)
area $F=d^2[\text{cm}]*\pi/4=3.142 \text{ cm}^2$ Embodiment 3

Two component material for temporary crowns and bridges, which is mixed in a ratio of 10/1 (base/catalyst) and cured without any smear layer.

The preparation is produced as described under embodiment 2.

|  | Gram, based on 100 g of paste: |
|---|---|
| Base paste: | |
| pyrogenic silicic acid (particle size < 0.05 micrometers) | 5.00 |
| glass powder, silanized (average particle size 10 micrometers) | 32.50 |
| 2,2-bis(4-(oligo(ethoxy))-phenyl)propanedimethacrylate | 49.00 |
| bisphenol-A-monoglycidether monomethacrylate (UVACURE 1561, company: UCB) | 12.00 |
| tributylborane* | 1.00 |
| diphenyliodonium-hexafluorophosphate (company: Avocado) | 0.50 |
| Catalyst paste: | |
| glass powder, silanized (average particle size 10 micrometers) | 32.00 |
| 2,2-bis(4-(oligo(ethoxy))-phenyl)-propane-diacetate | 65.00 |
| benzoylperoxide (peroxide chemistry) | 2.50 |

*Polymeric boron alkyl B2, prepared according to the data in Table B of the DE-A 3201780.

The use of the preparation, according to embodiment 3, results in a "total smear layer", for which a numerical value of <0.2 mg/cm$^2$ was found.

What is claimed is:

1. A dental material which cures to a solid through a cation chain mechanism, comprising:
    at least one ingredient selected from the group consisting of epoxide group containing monomers and epoxide group containing prepolymers;
    a first initiating system; and
    a second initiating system,
    wherein said first initiating system is comprised of at least one compound selected from the group consisting of boranes and hydrazones and releases species initiating a polymer forming reaction upon contact with oxygen,
    wherein said second initiating system is comprised of iodonium compounds capable of radical fission, and
    wherein said first initiating system and said second initiating system are present in an amount allowing for at least 10 seconds of oxygen contact before the dental material becomes a solid.

2. Dental materials, as claimed in claim 1, wherein the dental materials cure after contact with air.

3. Dental materials, as claimed in claim 1, wherein the dental materials contain double bond-containing monomers.

4. Dental materials, as claimed in claim 1, wherein the dental materials cure by means of a cationic ring opening polymerization.

5. Dental materials, as claimed in claim 1, wherein the dental materials contain epoxide group-containing monomers and at least one ingredient selected from the group consisting of double bond-containing monomers and double-bond containing prepolymers.

6. Dental materials, as claimed in claim 1, wherein the dental materials contain acryl group-containing monomers and prepolymers and cure by means of a radical chain mechanism.

7. Dental materials, as claimed in claim 1, wherein the dental materials contain allyl group-containing monomers and norbornene group-containing monomers and multi-thiol compounds and cure according to a thiolene mechanism.

8. Dental materials, as claimed in claim 1, wherein the dental materials contain diaryl iodonium compounds.

9. Process for curing dental materials, as claimed in claim 1, wherein prior to their application the dental materials are stored in light and oxygen proof containers, and wherein the dental material is removed from said container and brought into contact with the ambient air for a period ranging from 1 to 120 seconds.

10. Process for curing dental materials, as claimed in claim 1, wherein oxygen is produced in the dental materials by means of a chemical reaction with an oxygen releasing surface.

11. Process for curing dental materials, as claimed in claim 1, wherein prior to applying the dental material an oxygen releasing surface is produced by doping a surface with an oxygen rich material.

12. Process for curing dental materials, as claimed in claim 1, comprising:
    removing paste form dental materials from a container;
    applying the dental materials to a substrate using a hand tool within a range of 1 to 60 seconds; and
    exposing the dental materials to air, wherein upon exposure to air the dental materials cure to a new surface.

13. Process for curing dental materials, as claimed in claim 1, wherein the dental materials are treated with an air current following application.

14. Application of dental materials, as claimed in claim 1, for a use selected from the group consisting of: fastening crowns, fastening bridges, fastening inlays, filling cavities, treating mechanically prepared cavities, and treating cavities pretreated by means of an etching step.

15. A dental material which cures to a solid through a cation chain mechanism, comprising:
    at least one ingredient selected from the group consisting of epoxide group containing monomers and epoxide group containing prepolymers;
    a first initiating system; and
    a second initiating system,
    wherein said first initiating system is comprised of at least one compound selected from the group consisting of boranes and hydrazones and releases species initiating a polymer forming reaction upon contact with oxygen, wherein said second initiating system is comprised of iodonium compounds capable of radical fission, wherein said first initiating system and said second initiating system are present in an amount that allows the dental material to cure to a solid after contact with oxygen, and wherein the unpolymerized monomer layer on the surface is less than 0.2 mg/cm$^2$.

16. Dental materials, as claimed in claim 15, wherein the ratio of said first initiating system and said second initiating system is such that following contact with oxygen the dental materials can flow freely for at least 10 seconds and thereafter cure to a solid.

17. A kit, comprising: a container holding dental material, as claimed in claim 15.

18. A method of producing temporary crowns and bridges, comprising applying dental material according to claim 15 to a surface.

19. A curing material for polymer-forming preparations, comprising:

a first initiating system comprising an oxygen sensitive substance selected from the group consisting of boranes and hydrazones; and a second initiating system comprising at least one iodonium compound which decomposes under the influence of radicals and forms acids.

20. A curing material for polymer-forming preparations, as claimed in claim 19, wherein said second initiating system is a diaryl iodonium compound.

21. A curing material for polymer-forming preparations, as claimed in claim 19, wherein the polymer-forming preparation comprises epoxide-containing substances.

22. A method to set the processing time of a dental material, comprising application of a curing material for polymer-forming preparations according to claim 19.

23. The dental material of claim 1, further comprising at least one ingredient selected from the group consisting of fillers, dyes, flow modifiers, stabilizers, ion-transferring substances, x-ray opacity increasing compounds, and further modifiers.

24. The dental material of claim 15, further comprising at least one ingredient selected from the group consisting of fillers, dyes, flow modifiers, stabilizers, ion-transferring substances, x-ray opacity increasing compounds, and further modifiers.

25. A kit, comprising a container holding dental material according to claim 1.

* * * * *

UNITED STATES PATENT AND TRADEMARK OFFICE
CERTIFICATE OF CORRECTION

PATENT NO. : 6,652,281 B1
DATED : November 25, 2003
INVENTOR(S) : Eckhardt, Gunther It is certified that error appears in the above-identified patent and that said Letters Patent is hereby corrected as shown below:

Column 5,
Line 33, delete "prepared" and insert -- produced --, therefor.

Column 8,
Line 15, after "contain" insert -- mathacryl or --.
Line 19, delete "contain" and insert -- further comprise at least one ingredient selected from the group consisting of --, therefor.
Line 20, $1^{st}$ occurrence, delete "and" insert -- ; --, therefor.
Line 21, after "and" insert -- wherein the dental materials --.
Line 47, after "material" delete "cure to a" and insert -- form --, therefor.

Column 9,
Line 17, after "bridges" delete ",".

Signed and Sealed this

Twenty-seventh Day of September, 2005

JON W. DUDAS
*Director of the United States Patent and Trademark Office*